(12) United States Patent
Fish et al.

(10) Patent No.: US 10,047,024 B2
(45) Date of Patent: *Aug. 14, 2018

(54) PROCESS FOR THE PRODUCTION OF ETHYLENE, HYDROGEN CHLORIDE, AND VINYL CHLORIDE FROM ETHANE

(71) Applicant: Dow Global Technologies LLC, Midland, MI (US)

(72) Inventors: Barry B. Fish, Lake Jackson, TX (US); Matthew T. Pretz, Lake Jackson, TX (US); Max M. Tirtowidjojo, Lake Jackson, TX (US)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/525,348

(22) PCT Filed: Nov. 10, 2015

(86) PCT No.: PCT/US2015/059880
§ 371 (c)(1),
(2) Date: May 9, 2017

(87) PCT Pub. No.: WO2016/077300
PCT Pub. Date: May 19, 2016

(65) Prior Publication Data
US 2017/0334811 A1 Nov. 23, 2017

Related U.S. Application Data

(60) Provisional application No. 62/078,020, filed on Nov. 11, 2014.

(51) Int. Cl.
| | | |
|---|---|---|
| *C07C 17/10* | (2006.01) | |
| *C07C 5/44* | (2006.01) | |
| *C07C 21/06* | (2006.01) | |
| *C01B 7/01* | (2006.01) | |

(52) U.S. Cl.
CPC ............. *C07C 17/10* (2013.01); *C01B 7/01* (2013.01); *C07C 5/44* (2013.01); *C07C 21/06* (2013.01)

(58) Field of Classification Search
CPC ........... C07C 5/44; C07C 17/10; C07C 11/04; C07C 19/045
See application file for complete search history.

(56) References Cited

U.S. PATENT DOCUMENTS

| | | |
|---|---|---|
| 2,628,259 A | 2/1953 | Dirstine et al. |
| 3,879,482 A * | 4/1975 | Riegel ............... B01J 27/10 570/222 |
| 3,917,727 A | 11/1975 | Tsao |
| 5,097,083 A | 3/1992 | Stauffer |
| 5,705,728 A | 1/1998 | Viswanathan et al. |

FOREIGN PATENT DOCUMENTS

CA 2097434 A1 6/1992

* cited by examiner

*Primary Examiner* — Jafar F Parsa
(74) *Attorney, Agent, or Firm* — Tifani M. Edwards

(57) ABSTRACT

A process is provided for the chlorination of ethane using chlorine as the chlorinating agent to produce ethylene, hydrogen chloride (HCl) and vinyl chloride monomer (VCM).

11 Claims, 1 Drawing Sheet

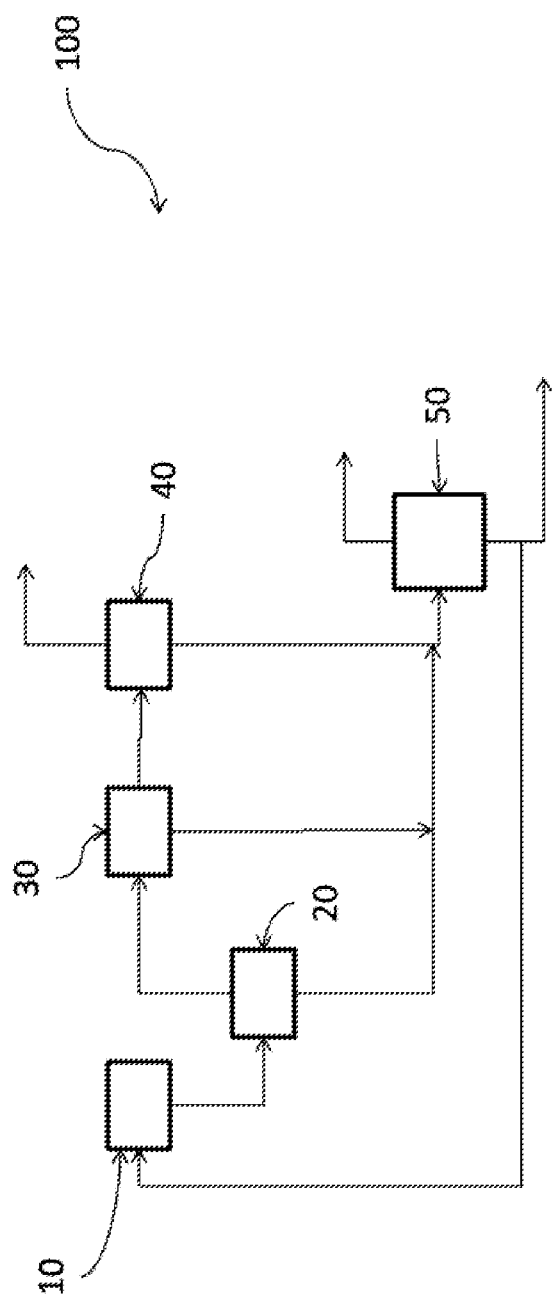

PROCESS FOR THE PRODUCTION OF ETHYLENE, HYDROGEN CHLORIDE, AND VINYL CHLORIDE FROM ETHANE

The present invention relates to a method of producing ethylene, hydrogen chloride (HCl), and vinyl chloride (VCM) by chlorinating ethane, using chlorine ($Cl_2$) as the chlorinating agent. The invention further relates to the partial recycling of heavies.

The foregoing products have traditionally been prepared from more expensive sources of hydrocarbons. Dating back to the early part of this century, the large scale production of vinyl chloride, trichloroethylene and perchloroethylene commenced with the use of acetylene however acetylene is a relatively expensive raw material. When the ethylene oxychlorination process was developed during the 1950's, acetylene was supplanted by less costly ethylene as a feedstock for chlorinated hydrocarbons. Up to the present time practically all chlorinated ethane/ethylene products have been derived from ethylene.

Although ethylene is produced in large quantities by world-scale plants, its cost is necessarily higher than the price of ethane from which it is preferentially made. Contributing to ethylene's cost is the necessity of employing complex, high-temperature cracking processes with inherent inefficiencies. Therefore, there would be a significant advantage of substituting ethane for ethylene in the manufacture of chlorinated ethane/ethylene. Particularly in the case of the manufacture of vinyl chloride, which requires about 0.45 pounds of ethylene per pound of product, any savings in the cost of hydrocarbon raw material would be important.

In order to circumvent the shortcomings of existing technology, numerous attempts have been made to chlorinate ethane by cost-effective means. One such method, for example, that employs various chlorinating agents including $C_2Cl_6$ combined with hydrogen chloride and chlorine is described in U.S. Pat. No. 5,097,083. While U.S. Pat. No. 5,097,083 demonstrated the use of $C_2Cl_6$ as a chlorinating agent, in some cases $C_2Cl_6$ may be unfavorable because additional operating and capital costs are needed to produce the chlorinating agent $C_2Cl_6$. For example, an oxychlorination reactor was proposed to chlorinate the $C_2Cl_4$ precursor for $C_2Cl_6$ and additional separation columns were needed to purify and recycle $C_2Cl_4$ and HCl. Another method, disclosed in U.S. Pat. No. 2,628,259 teaches chlorination of ethane to co-produce VCM and vinylidene chloride (1,1-dichloroethylene) and uses a high chlorine to ethane molar ratio that makes low selectivity to the desired products, VCM and ethylene. In contrast, CA2097434 teaches a process of high selectivity to ethylene by chlorination of ethane but at a lower than 1.1 molar ratio of chlorine to ethane that makes the process yield lower than 50% to the desired product.

It is therefore an object of the present invention to provide a method for the chlorination of ethane that overcomes the disadvantages of the conventional methods.

The present invention provides a continuous process for producing ethylene, hydrogen chloride and vinyl chloride monomer comprising
a) reacting a feed comprising chlorine with ethane in a reaction zone to produce a crude product wherein the crude product comprises
  i. product components comprising ethylene, vinyl chloride, and hydrogen chloride and
  ii. a partial recycle fraction comprising heavies;
b) fractionally separating from the crude product the partial recycle fraction; and
c) fractionally separating from the crude product the product components As used herein "adiabatic" means: the thermal chlorination process or reaction occurs without transfer of heat between the reactor and its surroundings. The process is said to be nearly adiabatic because the reactor is insulated or designed in such a manner that heat is not intentionally added or removed from the reactor.

As used herein "exit temperature" means: the temperature of reactor effluent. The chlorine to ethane feed ratio is one of the variables used to control the exit temperature. This chlorine:ethane molar ratio ranges from 1.1 to 2.0, alternatively from 1.1 to 1.9. The exit temperature ranges from 350-700° C., alternatively from 375-675° C., further alternatively from 400-650° C., and more preferably from 450-600° C.

As used herein "heavies" means: byproducts containing chloride that have a boiling point that is greater than the boiling point of VCM. The heavies of the present invention comprise primarily the following: 1,1,1-trichloroethane, 1,1-dichloroethylene, 1,1-dichloroethane, trans-1,2-dichloroethylene, cis-1,2-dichloroethylene, tetrachloroethanes, 1,1,2-trichloroethane, perchloroethylene. Heavies may also be produced by the process of the present invention and are fractionally separated from the crude product.

As used herein "inlet temperature" means: the mixed temperature of all the feed components streams as they enter the reactor wherein the feed components comprise ethane and/or partial recycle fraction and/or chlorine. The inlet temperature ranges from 200° C. to 350° C., alternatively from 210-330° C., further alternatively from 220-320° C., and more preferably from 230-300° C.

As used herein "partial recycle fraction" means: primarily the heavies.

As used herein "product components" means: primarily ethylene, HCl, and VCM.

All range values provided herein are inclusive and combinable. All percentages are percentages by weight. Primarily" is intended to mean greater than 80% by weight, alternatively greater than 85% by weight, further alternatively greater than 90% by weight.

FIG. 1 is a schematic view of the operation of a preferred embodiment of the process of the invention. Referring to the FIGURE, the process of the present invention is carried out as follows.

A feed containing components of ethane and chlorine is fed to a reactor (reactor is referred to as the "reaction zone"). The feed may be substantially free of ethylene, alternatively free of ethylene. The feed components may be preheated individually or in combination to the inlet temperature. The preheating of the feed components may occur in any manner and at any time prior to entry into the reactor 10. Prior art reference, CA 2097434 premixes ethane and chlorine below 200° C. and heats the mixture after adding it to the reactor. This method requires heat exchangers and thus is more capital intensive than the process of the present invention which uses a reactor 10 that is nearly adiabatic. Chlorine may be preheated to the inlet temperature or alternatively may comprise a temperature ranging from 20° to 80° C. before it is combined with the ethane and/or the partial recycle fraction. The chlorine may be co-fed into the reactor 10 with the ethane, mixed with the ethane and then added to the reactor 10, or added by other conventional means of introducing materials into a reactor.

Conventional reactors may be used. One suitable example of a reactor is a jet-stirred reactor. The temperature of the reactor 10 at the time of entry of feed ("inlet temperature")

ranges from 200-350° C., alternatively from 210-330° C., further alternatively from 220-320° C., and more preferably from 230-300° C. The thermal chlorination reaction is carried out in the reactor 10. The chlorine is highly reactive with the ethane and reacts to produce a crude product comprising product components and a partial recycle fraction. With the near adiabatic reactor condition, the exothermic reaction increases the crude product to a temperature higher than 350° C. up to 700° C. This crude product is cooled by heat exchanging with coolant or by adjusting feed ratios. This crude product leaving the heat exchanger contains both a vapor phase and a liquid reactor effluent.

The vapor phase and liquid reactor effluent are cooled further in a condenser 20 to condense the liquid. The liquid is provided preferably to a distillation column 40, or alternatively to a separation column 50. The vapor phase is compressed at a pressure greater than or equal to 689 kPa, alternatively greater than or equal to 1378 kPa and further alternatively greater than or equal to 1930 kPa in compressor 30 to enable efficient separation of ethylene and HCl from VCM in distillation column 40.

The distillation column 40 bottom stream is fed to the separation column 50 where VCM is stripped of heavies. Limits on distillation column 40 bottom temperature should be less than or equal to 150° C., alternatively less than or equal to 100° C. to minimize fouling/polymerization. The overhead stream of VCM can be purified to very high levels for sale or significant amounts of HCl can be allowed to slip out the bottom of distillation column 40 and be sent for further purification to an existing or new conventional VCM finishing plant. The use of a partial condenser on overheads of distillation column 40 is preferred in the separation of the HCl and ethylene mixture from VCM and the partial recycle fraction, since this provides a lower refrigeration load and hence lower operating cost as opposed to the use of total condenser.

This column 40 overhead stream comprising ethylene and HCl mixture can be further fed to an Oxychlorination reactor where HCl and ethylene are catalytically converted to EDC (Oxy EDC reactor) to produce EDC. Additional HCl and ethylene can be accordingly fed to this OxyEDC reactor to match the required reactant stoichiometry and thus lowering the raw material for the EDC production. Alternatively, additional HCl and/or ethylene can be fed to this OxyEDC reactor to increase the capacity in addition to the raw materials provided by the ethane chlorination process.

Furthermore, the overheads of distillation column 40 can be wholly or partially fed to an additional separation column or an HCl absorber to separate ethylene from HCL to enable use of the components independently. A portion of the bottom stream of separation column 50 comprising fractionally separated partial recycle fraction is recycled to the reactor zone 10. A portion of this partial recycle fraction can optionally also be recycled to quench unit 20 (not shown in the FIGURE). The rest of the separation column 50 bottom stream maybe further fed to other chlorination processes to produce trichloroethylene and perchloroethylene. Separation column 50 is operated such that less than 100 ppm of HCl is in overheads of separation column 50. More HCl impurity in the VCM stream from column 50 overheads could be included if the process is integrated with a conventional VCM plant with excess VCM finishing capacity.

Optionally, a single column could be used in place of distillation column 40 and separation column 50 to produce an overhead stream comprising an HCl/ethylene mixture, a mid column out stream comprising an HCl/VCM mixture, and a bottom stream comprising the partial recycle fraction. The process of the present invention is continuous.

The products produced by the present invention are valuable items of commerce. For example, vinyl chloride monomer is consumed in huge quantities in the manufacture of plastic materials. Furthermore, the reaction of the present invention is highly efficient as greater than 95%; alternatively greater than 99% of the chlorine is converted during the reaction. In addition, conversions of ethane greater than 90% and preferably greater than 95% are achieved. Unreacted ethane will ultimately be separated as part of the ethylene/HCL product and may be feed to an oxy EDC reactor. The unreacted ethane will pass through the oxy EDC reactor unreacted. This stream rich in ethylene could be sent through a polishing reactor such as liquid phase chlorination reactor to react any ethylene present to produce EDC.

EXAMPLE

Process for the Chlorination of Ethane

Ethane is chlorinated to produce ethylene, HCl, and VCM in a thermal chlorination jet-stirred reactor. The jet-stirred reactor is simulated as described elsewhere (see Chapter 8.7 in "Cleaner Combustion: Developing Detailed Kinetics Models," F. Battin-Leclerc, J. M. Simmie, E. Blurock (Ed) (2013)) using kinetics reported by Dahl et al. [Ind. Eng. Chem. Res. 2001, 40, 2226-2235]. The thermodynamic properties are obtained from reported literature values (see http://webbook.nist.gov/chemistry/) and thermochemical kinetics approach (see S. W. Benson "Thermochemical Kinetics: Methods for the Estimation of Thermochemical Data and Rate Parameters," 1976). The reactor model is imbedded inside a process flow sheet simulation (see http://www.aspentech.com/products/aspen-plus.aspx) such that impacts of recycle can be evaluated.

The reactor pressure of 40 psia and feed is preheated to higher than 200° C. and reactor exit temperature is maintained by adjusting chlorine flow rate. The residence time is about 0.5 sec to 1 second depending on whether outlet or inlet flow rate is used, respectively. Note that by preheating the feed components such that the mixed feed stream temperature as shown and maintaining $Cl_2$/ethane molar ratio of less than 1.9, the product yield to ethylene and VCM from ethane is greater than 80% as shown in table 1. This is much higher selectivity than previously reported (i.e. U.S. Pat. No. 2,628,259—table III) where only 60% selectivity to ethylene and VCM is obtained. With ethane conversion of greater than 95%, the results shown in Table 1 provides much higher total yield than those shown in CA2097434 where only 50% of ethane is converted.

TABLE 1

Process Operating Conditions and Product Unit Ratios

|  | Ex. 1 | Ex. 2 | Ex. 3 | Ex. 4 |
| --- | --- | --- | --- | --- |
| $Cl_2$/Ethane Molar Ratio | 1.37 | 1.25 | 1.43 | 1.62 |
| Partial Recycle Fraction/Fresh Ethane, mass ratio | 7.36 | 7.36 | 10.3 | 10.3 |
| Reactor Flow/Reactor Volume, kgmole/HR/m^3 | 236 | 228 | 281 | 291 |
| Inlet Temperature, ° C. | 284 | 285 | 281 | 280 |
| Exit Temperature ° C. | 524 | 499 | 494 | 529 |

TABLE 1-continued

Process Operating Conditions and Product Unit Ratios

|  | Ex. 1 | Ex. 2 | Ex. 3 | Ex. 4 |
|---|---|---|---|---|
| Chlorine Conversion | >99% | >99% | >99% | >99% |
| Ethane Conversion | 99% | 95% | 99% | >99% |
| Total Product composition, wt % | | | | |
| HCl | 68.6 | 69.0 | 67.4 | 67.2 |
| Other | 0.3 | 0.2 | 0.2 | 0.7 |
| Ethylene | 14.7 | 16.7 | 13.9 | 9.6 |
| VCM | 12.8 | 11.2 | 11.5 | 16.2 |
| Heavies | 3.6 | 2.9 | 7.0 | 6.3 |
| Product/ethane feed, mass ratio | | | | |
| HCl/Ethane | 2.9 | 2.68 | 2.95 | 3.25 |
| $C_2H_4$/Ethane | 0.62 | 0.65 | 0.61 | 0.47 |
| VCM/Ethane | 0.54 | 0.43 | 0.51 | 0.78 |
| Heavies/Ethane | 0.15 | 0.11 | 0.31 | 0.30 |
| Ethane yield to $C_2H_4$ & VCM Selectivity | 92% | 91% | 89% | 87% |
| Heavies composition, wt % | | | | |
| 1,1-dichloroethane | 0.4 | 0.8 | 0.9 | 0 |
| 1,1,1-trichloroethane | 7.2 | 7.1 | 11.7 | 4.6 |
| 1,1-dichloroethylene | 31.7 | 35.0 | 40.0 | 26.1 |
| Trans-1,2-dichloroethylene | 15.3 | 12.2 | 8.7 | 16.8 |
| Cis-1,2-dichloroethylene | 17.5 | 14.1 | 10.0 | 19.2 |
| Tetrachloroethanes | 0.7 | 1.0 | 1.7 | 0.4 |
| 1,1,2-trichloroethylene | 21.4 | 21.0 | 23.4 | 23.9 |
| perchloroethylene | 5.7 | 8.4 | 3.3 | 8.9 |

We claim:

1. A continuous process for producing ethylene, hydrogen chloride and vinyl chloride comprising
    a) reacting a feed comprising chlorine with ethane in a reaction zone at an inlet temperature from 230-300° C. to produce a crude product wherein the crude product comprises
        i. product components comprising ethylene, vinyl chloride, and hydrogen chloride and
        ii. a partial recycle fraction comprising heavies;
    b) fractionally separating from the crude product the partial recycle fraction; and
    c) fractionally separating from the crude product the product components
wherein greater than 95% of chlorine and ethane are converted into products.

2. The process of claim 1 wherein the reaction is conducted at near adiabatic condition.

3. The process of claim 1 further wherein the molar ratio of chlorine to ethane in the feed is greater than 1.1 but less than 2.0.

4. The process of claim 1 wherein the reactor comprises an exit temperature ranging from 350-700° C.

5. The process of claim 1 wherein the feed is pre-mixed prior to being fed in the reactor.

6. The process of claim 1 wherein the feed is not pre-mixed prior to being fed in the reactor and mixed as they entered the reactor.

7. The process of claim 1 wherein the HCl and ethylene are fractionally separated from the product components.

8. The process of claim 1 wherein the HCl and ethylene products are reacted in a downstream process to produce 1,2-dichloroethane.

9. The process of claim 1 wherein the heavies are further reacted to produce trichloroethylene, vinylidene chloride, and/or perchloroethylene.

10. The process of claim 1 wherein the partial recycle fraction is partially recycled to the reactor zone.

11. The process of claim 1 wherein the partial recycle fraction is partially recycled to quench the reactor effluent.

* * * * *